United States Patent [19]

Cheminal et al.

[11] Patent Number: 4,643,851
[45] Date of Patent: Feb. 17, 1987

[54] PROCESS FOR PREPARING TRIFLUOROACETYL CHLORIDE

[75] Inventors: Bernard Cheminal, Lyons; Henri Mathais, Saint-Didier-Au-Mont-D'or; Marc Thomarat, Pierre-Benite, all of France

[73] Assignee: Atochem, Courbevoie, France

[21] Appl. No.: 532,483

[22] Filed: Sep. 15, 1983

[30] Foreign Application Priority Data

Nov. 5, 1982 [FR] France .................. 82 18567

[51] Int. Cl.$^4$ ............................. C07C 51/58
[52] U.S. Cl. .................... 260/544 Y; 260/694
[58] Field of Search .......... 260/544 Y, 544 C, 544 M, 260/694; 502/180

[56] References Cited

U.S. PATENT DOCUMENTS 2,922,816  1/1960  MacMillan .................. 260/544 F

FOREIGN PATENT DOCUMENTS 515963  12/1939  United Kingdom .
1056512  1/1967  United Kingdom .

OTHER PUBLICATIONS

Patai, Saul *The Chemistry of Acyl Halides* (1972) Interscience, Publ. pp. 55–57.
Kato, Yogoro Chemical Abstracts vol. 43 (1939) #3027h.
Clark, N. G. *Modern Organic Chemistry* (1964) Oxiford Univ Press, Publ. pp. 514–515.
Association Institut du pin Chemical Abstracts vol. 47 (1953) #8362c, (French 980,300).

*Primary Examiner*—Natalie Trousof
*Assistant Examiner*—L. Hendriksen
*Attorney, Agent, or Firm*—Pennie & Edmonds

[57] ABSTRACT

The invention relates to the preparation of trifluoroacetyl chloride by catalytic chlorination of trifluoroacetaldehyde with chlorine. Catalysis is performed in the vapor phase in a fixed bed or a fluidized bed reactor with an activated carbon catalyst. Optionally, hydrochloric acid and/or an inert diluent can be present with the reactant without affecting the results of this process.

17 Claims, No Drawings

PROCESS FOR PREPARING TRIFLUOROACETYL CHLORIDE

TECHNICAL FIELD

This invention relates to the preparation of trifluoroacetyl chloride by catalytic chlorination of trifluoroacetaldehyde (fluoral) with chlorine. More particularly, trifluoroacetyl chloride is prepared by chlorination of fluoral with chlorine in the gaseous phase on an active carbon catalyst.

BACKGROUND OF THE INVENTION

Trifluoroacetyl chloride is a known commercially useful compound that can be used to synthesize important industrial products. For example, it can be hydrolyzed according to known techniques to obtain trifluoroacetic acid which then can be used either as a dimerization catalyst of unsaturated aliphatic hydrocarbons in the production of pharmaceutical products or as the active ingredient in pesticide formulations.

It is known that trifluoroacetyl chloride can be synthesized by noncatalytic processes. French Pat. No. 2,226,380 describes the synthesis of trifluoroacetyl chloride by subjecting 1,1-dichlorotrifluoroethane and oxygen in the gaseous phase to ultraviolet radiation. This process requires extensive safety measures to avoid the danger of explosion, highly complex photochemical equipment, and large amounts of light and caloric energy. In addition to these drawbacks, the process produces a relatively low yield of trifluoroacetyl chloride.

French Pat. No. 1,385,111 discloses a process for photochemical chlorination of pure liquid fluoral at about −30° C. in the presence of ultraviolet light. This method cannot be used commercially because fluoral polymerizes so rapidly that storage of this material is difficult. Also, the process of the French patent does not provide a satisfactory reaction rate or a sufficiently high yield.

It is also known that trifluoroacetyl chloride can be synthesized catalytically from compounds other than fluoral. For example, French Pat. No. 2,038,257 describes the catalytic oxidation of 1,1,1-trichlorotrifluoroethane with sulfur trioxide. This process has two disadvantages; the use of toxic catalysts with a mercuric sulfate base and the formation of a troublesome sulfuryl chloride byproduct.

French Pat. No. 2,169,221 relates to a process for preparing trifluoroacetic acid, one step of which consists of catalytically transforming trifluoroacetyl fluoride into trifluoroacetyl chloride in the presence of carbon tetrachloride, chloroform, or trichlorofluoro methane. This method has the disadvantage of inevitably forming byproducts such as, for example, trichlorofluoro methane when carbon tetrachloride is used.

DISCLOSURE OF THE INVENTION

The process of the present invention makes it possible to overcome the disadvantages and drawbacks of these known techniques. To accomplish this, trifluoroacetyl chloride is prepared by chlorination of fluoral with chlorine in the gaseous phase in the presence of an active carbon catalyst.

Unlike the prior art, this process makes it possible to obtain a substantially complete conversion of fluoral and high yields of trifluoroacetyl chloride.

The starting product can be pure fluoral or fluoral hydrochloride. With either compound, diluents such as gaseous hydrochloric acid and/or inert gases such as nitrogen or chlorotrifluoromethane can be used.

The hydrochloric acid/fluoral molar ratio can range from 0 to 5, and the inert diluent/fluoral molar ratio can also range from 0 to 5. When the hydrochloric acid and inert diluent are both present, the sum of the molar ratios of hydrochloric acid/fluoral and inert diluent/fluoral should not be greater than 5. By way of example, the inert diluent/fluoral ratio is preferably 3 to 4 when the hydrochloric acid/fluoral molar ratio is about 1. As mentioned above, the preferred inert gas diluents are nitrogen or chlorotrifluoromethane.

The chlorine/fluoral molar ratio is generally in the range of 1 to 2, and the reaction temperature advantageously ranges from 130° to 250° C. The reaction can be performed at atmospheric pressure or above, and preferably is between 1 and 5 bars absolute.

The reaction can be performed in either a fixed or fluidized bed reactor. When a fixed bed reactor is used, the contact time generally ranges from 5 to 30 seconds. The contact time is defined as the time (in seconds) required to introduce a volume of reactants into the reactor equal to the apparent volume of the catalyst measured under normal temperature and pressure conditions.

When the reaction is performed in a fluidized bed reactor, the velocity of the gases of the reactants entering the reaction zone is such that it corresponds to a delivery rate equal to approximately 1.5 to 3 times the minimum fluidizing delivery rate of the catalyst. The preferred catalyst is selected from the family of active carbons.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

Examples: The scope of the invention is further described in connection with the following examples which are set forth for purposes of illustration only and are not to be construed as limiting the scope of the invention in any manner.

For each of the tests described, the gaseous mixture leaving the reactor is analyzed by gaseous chromatography on a silicone phase after neutralizing any remaining hydrochloric acid with dibasic sodium phosphate.

EXAMPLE 1

300 ml of an active carbon catalyst (supplied by the NORIT company) having a specific surface area of 947 $m^2/g$, and a porous volume of 0.59 cc/g in the form of 0.8 mm grains are placed in a reactor comprised essentially of an Inconel pipe 40 mm in diameter with 240 mm of useful height. The reactor is then heated to 300° C.

After nitrogen drying at 300° C., 0.577 mole/h of chlorine is passed over the catalyst for an hour. A gaseous mixture containing 1.28 moles/of chlorine and 4.93 moles of hydrochloric acid per mole of fluoral is then introduced into the reactor at a rate of 48.5 Nl/h. The reactor is operated at atmospheric pressure and 185° C.

The rate of conversion of fluoral is 51% and the molar yield of trifluoroacetyl chloride in relation to the transformed fluoral was found to be 85.3%.

EXAMPLE 2

The equipment of Example 1 is operated with the same catalyst as in Example 1, except that only 100 ml of catalyst is used and the reactor temperature is held at 136° C. A mixture of 1.4 moles chlorine and 1.22 moles hydrochloric acid per mole of fluoral is introduced into the reactor at a rate of 10 Nl/h. The rate of transformation of the fluoral is found to be 80% and the yield of trifluoroacetyl chloride found to be 60%.

EXAMPLE 3

300 ml of the active carbon catalyst of Example 1, this time in the form of grains of 125 to 210 μm, is introduced into the equipment of Example 1. A gas flow distribution system is used at the base of the reactor to assure proper fluidizing of the catalyst. A gaseous mixture containing 1.3 moles of chlorine, 1 mole hydrochloric acid, and 3 moles nitrogen per mole of fluoral is introduced into the reactor at a rate of 32.8 Nl/h.

The reaction is performed at a temperature of 190° C., and the rate of conversion of the fluoral is 98.6% and the yield of trifluoroacetyl chloride 92.1%.

EXAMPLE 4

The same conditions as in Example 3 are used except that the molar ratios of chlorine/fluoral and nitrogen/fluoral are 1.90 and 3.65 respectively. The conversion of fluoral is 100% and the yield of trifluoroacetyl chloride 93.2%.

EXAMPLE 5

The same equipment and catalyst as in Example 3 are operated at 188° C. The reactants, are 1.43 moles chlorine and 4.76 moles hydrochloric acid per mole of fluoral, which is introduced into the reactor at a rate of 4.12 Nl/h. The conversion of fluoral was found to be 99% and the yield of trifluoroacetyl chloride 88.3%.

EXAMPLE 6

In the equipment of Example 3, operated at 220° C. with 0.3 liter of the same catalyst, the reactants, are 1.32 moles chlorine, 1 mole hydrochloric acid, and 3.68 moles of nitrogen per mole of fluoral, which is introduced into the reactor at a rate of 4.26 Nl/h. The conversion of the fluoral is 100% and the yield of trifluoroacetyl chloride 94.2%.

EXAMPLE 7

When operating at 210° C. with the same catalyst and equipment as in Example 3, the reactants, are 1.4 moles chlorine, 1 mole hydrochloric acid, and 3.3 moles chlorotrifluoro methane per mole of fluoral, which is introduced into the reactor at a rate of 0.203 mole per hour. The conversion of fluoral is 100% and the yield of trifluoroacetyl chloride, 96.9%.

We claim:

1. A continuous process for preparing trifluoro acetyl chloride which comprises reacting trifluoroacetaldehyde (fluoral) and chlorine in the vapor phase by passing a gaseous mixture of trifluoro acetaldehyde (fluoral), chlorine, and hydrochloric acid through a fluidized bed reactor containing an active carbon catalyst at a temperature range of between about 130° and 250° C. and at a delivery rate sufficient to assure fluidizing of the active carbon catalyst.

2. The process according to claim 1 wherein the chlorine/fluoral molar ratio ranges from between about 1 and 2.

3. The process according to claim 1 wherein said delivery rate provides a hydrochloric acid/fluoral molar ratio of between about 1 and 5.

4. The process according to claim 1 wherein said chlorination is performed in the presence of an amount of inert diluent such that the inert diluent/fluoral molar ratio is between about zero and 5.

5. The process according to claim 1 wherein said chlorination is performed in the presence of amounts of hydrochloric acid and inert diluent such that the sum of the molar ratios of hydrochloric acid/fluoral and inert diluent/fluoral is not greater than about 5.

6. The process according to claim 4 wherein the inert diluent is nitrogen or chlorotrifluoromethane.

7. The process according to claim 5 wherein the inert diluent is nitrogen or chlorotrifluoromethane.

8. A continuous process for preparing trifluoracetyl chloride consisting essentially of reacting a gaseous mixture of trifluoro acetaldehyde (fluoral), chlorine and hydrochloric acid in the presence of an inert diluent and an active carbon catalyst in a fluidized bed reactor at a temperature range of about 130° to 250° C. wherein the gaseous trifluoroacetaldehyde (fluoral) chlorine and hydrochloric acid are delivered to the reactor in such proportions that:
 (a) the chlorine/fluoral molar ratio is between about 1 and 2;
 (b) the hydrochloric acid/fluoral molar ratio is between about 1 and 5;
 (c) the inert diluent/fluoral molar ratio is not greater than about 4; and
 (d) the sum of the molar ratios of hydrochloric acid/fluoral and inert diluent/fluoral is not greater than about 5.

9. The process according to claim 8 wherein the reaction is performed in a fluidized bed reactor with the velocity of the reactant gases entering the reaction zone corresponding to a delivery rate of between about 1.5 and 3 times the minimum delivery rate to fluidize the catalyst.

10. A continuous process for the preparation of trifluoroacetyl chloride by chlorination of trifluoroacetaldehyde (fluoral) with chlorine, wherein said chlorination is performed at a temperature range of between about 130° and 250° C. in the vapor phase and in a fluidized bed reactor containing an active carbon catalyst, by passing through said reactor a gaseous mixture of trifluoroacetaldehyde (fluoral), chlorine and hydrochloric acid at a delivery rate sufficient to assure fluidizing of the active carbon catalyst and in such proportions that the chlorine/fluoral molar ratio is between about 1 and 2 and the hydrochloric acid/fluoral molar ratio ranges from 1 to 5.

11. The process according to claim 10 wherein the reaction pressure is between about 1 and 5 bars absolute.

12. The process according to claim 10 wherein the velocity of the gaseous mixture entering the reactor corresponds to a delivery rate of between about 1.5 and 3 times the minimum delivery rate to fluidize the catalyst.

13. The process according to claim 10 wherein the gaseous mixture further comprises an inert diluent in an amount such that the hydrochloric acid plus inert diluent/fluoral molar ratio is not greater than about 5.

14. The process according to claim 13 wherein the reaction is performed in a fluidized bed reactor with the velocity of the reactant gases entering the reaction zone corresponding to a delivery rate of between about 1.5 and 3 times the minimum delivery rate to fluidize the catalyst.

15. The process according to claim 13 wherein the inert diluent is nitrogen or chlorotrifluoro methane.

16. The process according to claim 13 wherein said inert diluent/fluoral ratio is about 3 to 4 and the hydrochloric acid/fluoral ratio is about 1.

17. The process according to claim 13 wherein the reaction pressure is between about 1 and 5 bars absolute.

* * * * *